US00PP22630P2

(12) United States Plant Patent
van Dijk

(10) Patent No.: US PP22,630 P2
(45) Date of Patent: Apr. 3, 2012

(54) *ANTHURIUM* PLANT NAMED 'ANTHUCOEN'

(50) Latin Name: ***Anthurium andreanum* L.**
Varietal Denomination: Anthucoen

(75) Inventor: Jan van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 13/068,136

(22) Filed: May 3, 2011

(51) Int. Cl.
*A01H 5/00* (2006.01)

(52) U.S. Cl. ..... Plt./368; Plt./365

(58) Field of Classification Search ..... Plt./368, Plt./365
See application file for complete search history.

(56) References Cited

OTHER PUBLICATIONS

UPOV-ROM Plant Variety Database, PBR 20072710, published Feb. 15, 2008 in the European Community, one page.*

* cited by examiner

*Primary Examiner* — June Hwu
*Assistant Examiner* — Louanne Krawczewicz Myers
(74) *Attorney, Agent, or Firm* — Jondle & Associates, P.C.

(57) ABSTRACT

A new *Anthurium* plant particularly distinguished by having durable red-purple spathes that very slowly turn green with age, dark green durable glossy leaves, very rich and early flowering throughout the year, a long erect penduncle, rich shoot formation, a compact and full plant habit and a plant height of 35.0 cm to 45.0 cm, is disclosed.

3 Drawing Sheets

Genus and species: *Anthurium andreanum* L.
Variety denomination: 'Anthucoen'.

BACKGROUND OF THE NEW PLANT

The present invention comprises a new and distinct variety of *Anthurium*, botanically known as *Anthurium andreanum* L., and hereinafter referred to by the variety name 'Anthucoen'. The new variety originated from a hybridization made in December 2001 in Bleiswijk, The Netherlands. The female parent was the red *Anthurium* pot plant 'Anthepedi' (U.S. Plant Pat. No. 18,644), while the male parent was the white *Anthurium* plant '3644-01' (unpatented).

A single plant was selected in October 2003 and has been asexually reproduced repeatedly by tissue culture in Bleiswijk, The Netherlands over a five-year period. The new variety has been found to retain its distinctive characteristics through successive asexual propagations.

Plant Breeder's Rights for this variety were applied for in the European Union on Nov. 30, 2007, in Japan on Mar. 9, 2010. 'Anthucoen' has not been made publicly available or sold anywhere in the world for more than one year prior to the filing of this application.

SUMMARY OF THE INVENTION

The following are the most outstanding and distinguishing characteristics of this new variety when grown under normal horticultural practices in Bleiswijk, The Netherlands.

1) Purple-pink colored medium sized spathe;
2) Purple spadix;
3) Rich shoot formation; and
4) Compact plant habit.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 48-week old plant grown in a greenhouse in Bleiswijk, The Netherlands in 2009.

DESCRIPTION OF THE NEW VARIETY

Figure 1:
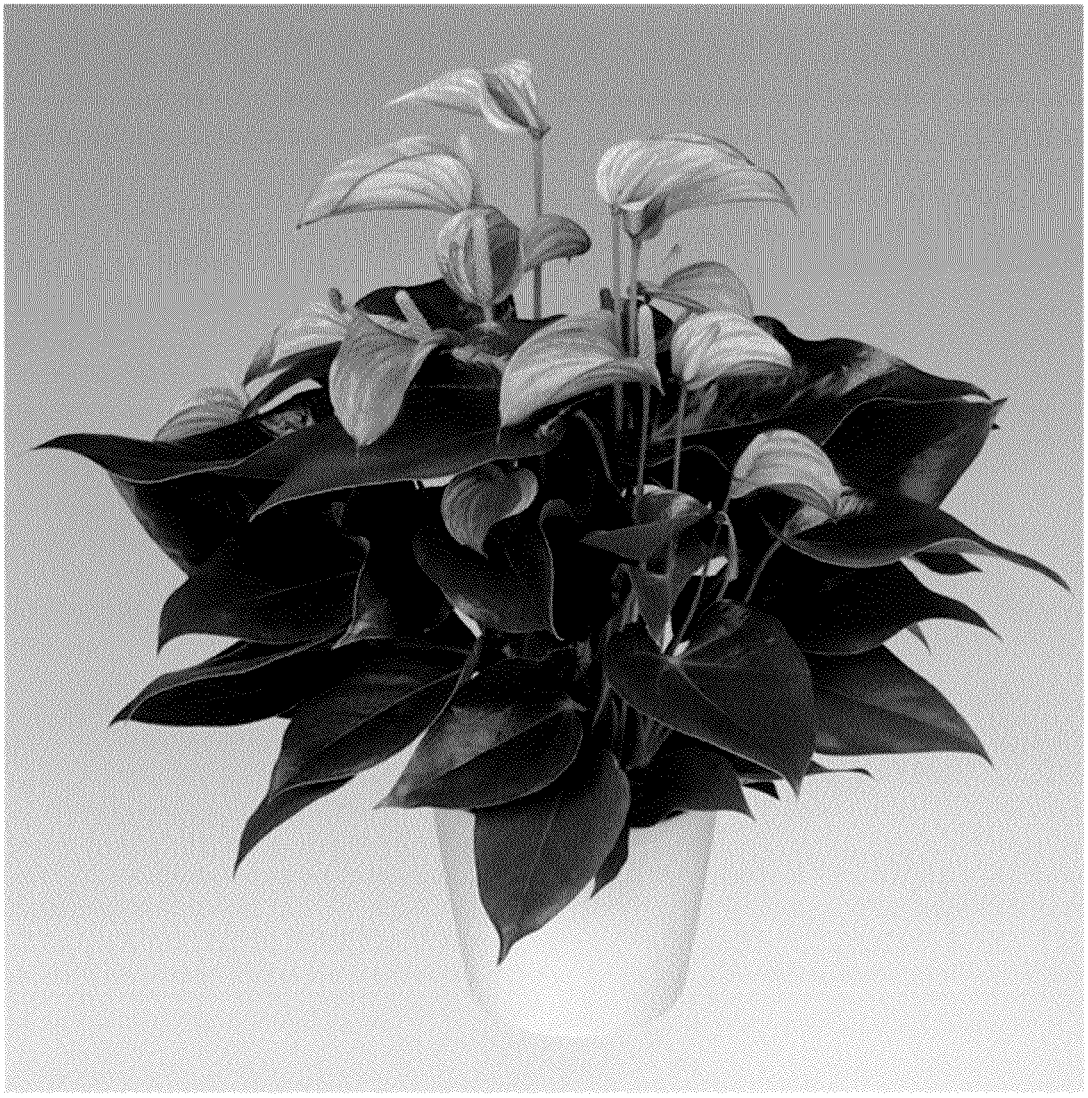
FIG. 1 shows the overall plant habit, including blooms, buds and foliage.
Figure 2:
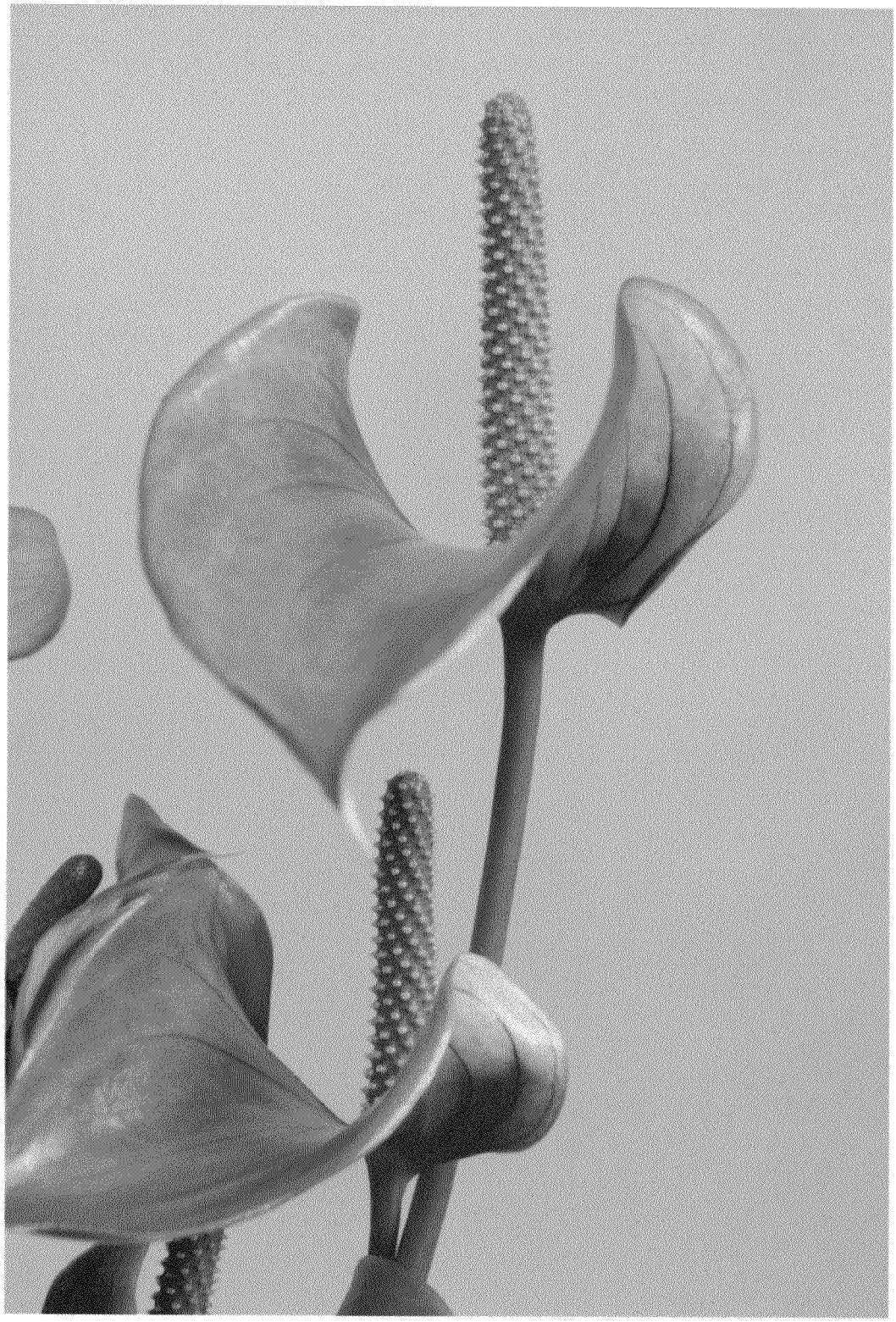
FIG. 2 is a close-up of the mature spathe.
Figure 3:
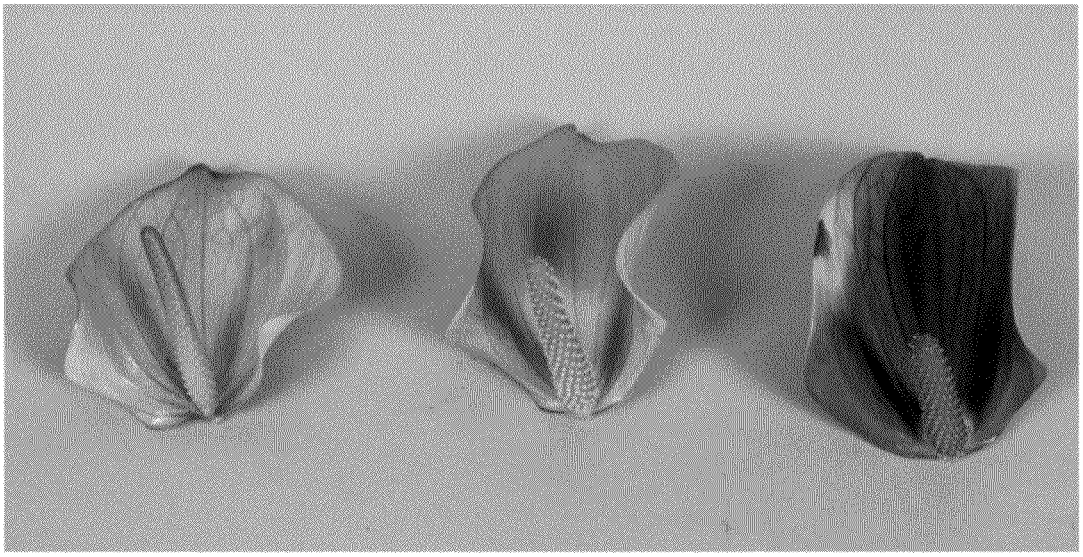
FIG. 3 shows three spathes at different stages of development, from left to right: just unfurled, 8 weeks, and approximately 30 weeks.
Figure 4:
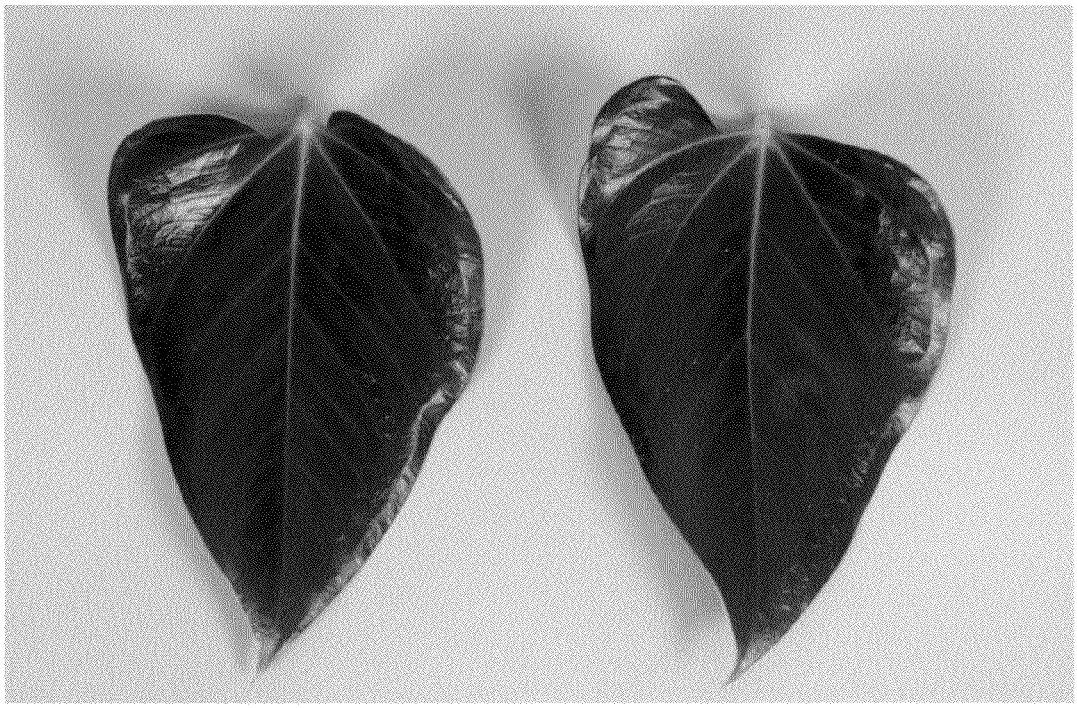
FIG. 4 shows the upper leaf surfaces: left side, 10 weeks old and right side, just unfurled.

The following detailed description sets forth the distinctive characteristics of 'Anthucoen'. The data which define these characteristics were collected from asexual reproductions carried out in Bleiswijk, The Netherlands. The plant history was taken on 48-week old plants which were planted from tissue culture in 17 centimeter pots and grown in a glass greenhouse between 19° C. and 24° C. Observations were made in November of 2009. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:
*Family.*—Araceae.
*Botanical.*—*Anthurium andreanum* L.
*Common name.*—*Anthurium.*

Parentage:
*Female parent.*—*Anthurium* plant 'Anthepedi' (U.S. Plant Pat. No. 18,644).
*Male parent.*—*Anthurium* plant '3644-01' (unpatented).

Plant:

*Propagation*.—Tissue culture.

*Root description*.—Fleshy cream-colored roots with smaller hairy lateral roots having yellow-colored root tips.

*Time to produce a finished flowering plant*.—45 to 50 weeks for a 17 cm pot.

*Growth habit*.—Herbaceous perennial.

*Height* (*measured from soil, including inflorescence*).—35.0 cm to 45.0 cm.

*Width* (*measured from leaf tips*).—40.0 cm to 50.0 cm.

Leaves:

*Immature leaves*.—Length: 4.0 cm to 11.0 cm. Width: 4.0 cm to 7.0 cm. Color: Upper surface: RHS 137A. Lower surface: RHS 137C. Texture: Shiny (on both surfaces).

*Mature leaves*.—Length (fully expanded): 15.0 cm to 18.0 cm. Width: 10.0 cm to 12.0 cm. Shape: Elliptical-subcordate, weakly cupped. Apex: Acuminate. Base: Subcordate. Leaf blade angle with the petiole: Between 120 degrees and 150 degrees. Leaf margin: Entire. Color: Upper surface: RHS 139A. Lower surface: RHS 137C. Texture (both surfaces): Shiny, leathery and thick; not blistered. Venation: Pinnate with protruding primary and mid-veins at the underside of the leaf blade. Venation color: Upper surface: RHS 137C. Lower surface: RHS 147C.

*Lobes*.—Arrangement: Leaf blade has two large lobes extending past the petiole. Length of lobes of mature leaf blades: 1.0 cm to 2.0 cm. Width of lobes of mature leaf blades: 5.0 cm to 6.0 cm. Distance for petiole/leaf junction to highest point on lobes of mature leaf blades: 3.5 cm to 4.0 cm.

*Petiole*.—Cross-section: Round. Diameter: 0.3 cm to 0.4 cm. Length: 10.0 cm to 13.0 cm for a mature leaf size. Color: Mature leaf: RHS 146B. Immature leaf: RHS 146D. Cataphyl color surrounding the petiole: Outside: RHS 146D. Inside: RHS 145C to RHS 146C.

*Geniculum*.—Length: 1.5 to 2.0 cm. Width: 0.4 cm to 0.5 cm. Color: RHS 146B.

Inflorescence:

*Arrangement*.—Single.

*Flowering habit* (*length of flowering season*).—Continuous.

*Number of inflorescences per plant*.—12 to 16.

*Fragrance*.—Absent.

*Longevity of inflorescence on plant*.—Greater than a year.

*Longevity of the flower as a cut flower*.—Not observed.

Spathe:

*Buds*.—The spathe is tightly rolled around the spadix and extrudes from the peduncle sheath. After the spathe is fully opened the peduncle elongates some extra centimeters.

*Arrangement*.—Spathe angle with the peduncle is between 80 degrees and 120 degrees; the spathe stands on a wiry peduncle about 5.0 cm to 9.0 cm above the foliage.

*Shape*.—Oblong with a flat (not blistered) surface.

*Apex*.—Acuminate.

*Base*.—Obtuse.

*Texture*.—Shiny; unblistered.

*Margin*.—Entire.

*Size*.—Height: 18.0 cm to 25.0 cm (Peduncle length at maturity). Length: 6.0 cm to 10.0 cm. Width: 6.0 cm to 8.0 cm.

*Color*.—Just fully open: Upper surface: RHS 59D with little amount of green towards the lobes (up to RHS 143A). Lower surface: RHS 186C with a little amount of green towards the lobes. At 6 to 8 weeks after opening: Upper surface, RHS 184C and in the lobes at the base RHS 138A; Lower surface: 186C. At 12 to 14 weeks after opening: Upper surface, The primary color remains RHS 184C in the central part of the spathe, but the veins in the spathe slowly turn dark and the amount of green in the spathe slowly increases; Lower surface, RHS 186C.

Peduncle:

*Shape*.—Erect.

*Cross-section*.—Round.

*Length*.—18.0 cm to 25.0 cm.

*Diameter*.—0.2 cm to 0.4 cm.

*Color*.—RHS 146B at unrolling of spathe, slowly turning RHS 138A when the spathe matures.

Flowering time:

*General*.—One small rooted untreated tissue culture plant of 2 cm tall will flower, depending on season, after 5 to 7 months and 2 to 3 blossoms appear. More blossoms appear after some additional weeks so that a full flowering commercial plant will have 12 to 16 purple spathes. Smaller blossoms may occur on less mature plants.

Spadix:

*Size*.—Length: 2.0 cm to 5.0 cm (depending on flower size). Width (at apex): 0.4 cm to 0.7 cm. Width (at base): 0.4 cm to 0.8 cm.

*Shape*.—Columnar.

*Angle of spadix tip with peduncle*.—180 degrees (spadix is in one line with peduncle).

*Texture*.—When the spathe is unfurling the spadix is smooth. When the spadix matures, very small stigmata protrude. The stigmata are evenly distributed round the spadix. The spadix matures from base to top, slowly giving the spadix a somewhat rough appearance.

*Color*.—Immature: RHS 182D (no gradient). Mature: RHS 84C. Ages to: RHS 146A.

Flowers:

*Quantity per spadix*.—200 to 250.

*Spadix flower arrangement*.—Bisexual, rounded in cross-section.

*Shape*.—Rounded.

*Size*.—Length: 0.1 cm to 0.2 cm. Diameter (maximum): 0.2 cm.

*Color*.—RHS 84C.

Reproductive organs:

*Stamens*.—None visible.

*Pollen*.—Sparse.

*Pollen color*.—RHS 156D.

*Pistil*.—Quantity: Many. Length: Less than 0.01 cm. Color: RHS 84C. Style: None observed. Stigma: Shape: Ovoid. Diameter: Less than 0.01 cm. Color: RHS 84C. Ovary: Rarely visible. Ovary color: RHS 155A.

Fruit and seed set: None observed.

COMPARISON WITH PARENTAL AND COMMERCIAL VARIETIES

'Anthucoen' differs from the female parent and commercial variety 'Anthepedi' (U.S. Plant Pat. No. 18,644), in that 'Anthucoen' has purple colored spathes, whereas 'Anthepedi' has red colored spathes. Additionally, the spathes of 'Anthepedi' are blistered, whereas the spathes of 'Anthucoen' are unblistered.

'Anthucoen' differs from the male parent '3644-01' (unpatented), by having a purple colored spathe, smaller leaves and more basal branching, whereas '3644-01' has a white spathe.

'Anthucoen' is comparable to the commercially available variety 'Pink Champion' (U.S. Plant Pat. No. 12,115). 'Anthucoen' differs from 'Pink Champion' in that 'Anthucoen' has purple colored spathes, while 'Pink Champion' has pink spathes.

TABLE 1

Comparison of characteristics between 'Anthucoen', 'Anthepedi' and 'Pink Champion'

| Characteristic | 'Anthucoen' | 'Anthepedi' | 'Pink Champion' |
|---|---|---|---|
| Spathe color | RHS 184C | RHS 45B | RHS 52B |
| Spadix color | RHS 84C | RHS 155A | RHS 48B |
| Leaf length | 15.0-18.0 cm | 17.0-21.0 cm | 15.0-18.0 |
| Spathe blistering | Absent | Present | Absent |
| Plant height at maturity | 35.0-45.0 cm | 35.0-45.0 cm | 40.0-50.0 cm |

I claim:

1. A new and distinct variety of *Anthurium* plant named 'Anthucoen' as shown and described herein.

* * * * *